United States Patent [19]

Green

[11] Patent Number: 4,474,744
[45] Date of Patent: Oct. 2, 1984

[54] PROCESS FOR THE DECARBONYLATION OF AN ALKYL FORMATE TO FORM CARBON MONOXIDE AND AN ALCOHOL

[75] Inventor: Michael J. Green, Hull, England

[73] Assignee: BP Chemicals Limited, London, England

[21] Appl. No.: 569,396

[22] Filed: Jan. 9, 1984

[30] Foreign Application Priority Data

Jan. 19, 1983 [GB] United Kingdom ................. 8310464

[51] Int. Cl.$^3$ ....................... C01B 31/18; C07C 31/04
[52] U.S. Cl. ................................ 423/415 A; 568/876
[58] Field of Search ................... 423/415, 247, 415 A; 568/876

[56] References Cited

U.S. PATENT DOCUMENTS 3,812,210 5/1974 Higdon et al. ...................... 568/876
4,303,630 12/1981 Sano et al. ........................ 423/415 A
4,319,050 3/1982 Doyle .............................. 568/876 X Primary Examiner—Earl C. Thomas
Attorney, Agent, or Firm—Brooks, Haidt, Haffner & Delahunty

[57] ABSTRACT

An alcohol and carbon monoxide are produced by the decarbonylation of an alkyl formate in the presence of, as catalyst, (i) a Lewis base and epoxide or (2) an amidine or a guanidine. When the Lewis base used is a trivalent phosphorus compound, for example a phosphine, it is preferable to have alcohol present at the start of the reaction.

11 Claims, No Drawings

PROCESS FOR THE DECARBONYLATION OF AN ALKYL FORMATE TO FORM CARBON MONOXIDE AND AN ALCOHOL

This invention relates to a process for the decarbonylation of an alkyl formate to an alcohol and carbon monoxide.

In our copending European patent application No. 83305550.2 there is described a process for the preparation of alkyl formates from carbon monoxide and alcohols using as catalysts amidines or guanidines which can optionally be promoted by an epoxide.

It has been found that the above described catalysts are also effective for the decarbonylation of formates to form carbon monoxide and an alcohol and that in the presence of an epoxide, the reaction can be catalysed not only by amidines and guanidines but by other Lewis bases.

Thus, according to the present invention a process for the decarbonylation of an alkyl formate to form carbon monoxide and an alcohol comprises decarbonylating the alkyl formate at elevated temperature in the presence of:

(a) a Lewis base and an epoxide or
(b) an amidine.

The term Lewis base is well known and refers to a compound containing an unshared pair of electrons capable of sharing with an acid. The terms Lewis base and amidine are not therefore mutually exclusive.

The Lewis base can be an organic compound containing trivalent nitrogen or phosphorus for example an amine or phosphine.

By the term amidine is meant a compound containing the grouping

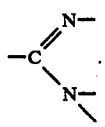

Conveniently the free valencies on the nitrogen atoms are attached to carbon atoms or hydrogen and the free valency on the carbon to another carbon atom or nitrogen atom. In the last mentioned case the structure will comprise a guanidine grouping.

A preferred glass of amidines is the cyclic amidines. Cyclic amidines are defined as those amidines wherein at least one of the nitrogen atoms is part of an alicyclic or heterocyclic substituted or unsubstituted hydrocarbyl ring. In the case where the amidine is a guanidine then any two of the three nitrogen atoms may be in the same or different rings. Those nitrogen atoms which are not part of any said ring may form part of a substituted or unsubstituted hyrocarbyl group.

A preferred class of cyclic amidine is that in which the amidine group can form part of a fused ring system containing 6 and 5 membered rings or 6 and 7 membered rings or two six membered rings, as for example in 1,5-diazabicyclo[4.3.0]non-5-ene which has the formula

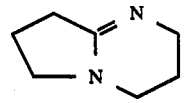

or 1,8-diazabicyclo[5.4.0]undec-7-ene of the formula

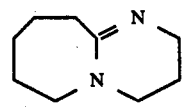

or 1,5,7-triazabicyclo[4.4.0]dec-5-ene of formula

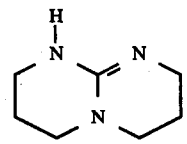

The epoxide is preferably a lower alkylene oxide such as ethylene oxide, propylene oxide or butylene oxide.

Preferably the molar proportions of Lewis base to epoxide are in the range 1:0.5 to 1:5.

The amount of catalyst mixture is preferably from 0.01 to 50% more preferably from 0.1 to 20% by weight based on the weight of reactants.

Where the Lewis base used as a catalyst is a trivalent phosphorus compound, it is preferable to have an alcohol present at the start of the process.

Conveniently the process is carried out under superatmosphericpressure, for example, 1 to 150 bar and elevated temperature, for example in the range 50° to 200° C.

The alkyl formate is conveniently one which yields an alkanol or an aralkyl alcohol e.g. benzyl alcohol. The term alkyl in the present specification is therefore intended to include aralkyl.

Preferably the alkyl formate is one which yields a primary lower aliphatic alcohol, for example methanol, ethanol, n-butanol.

The invention is illustrated by the following examples which were effected with the formate starting material and alcohol product in the liquid phase.

EXAMPLE 1

A 100 ml high pressure stirred autoclave was charged with 30 g of methyl formate and 2 g of 1,5,7-triazabicyclo[4.4.0]dec-5-ene (TBD). The autoclave was sealed and flushed twice with nitrogen, following which it was pressurised to 14 bar with nitrogen and finally heated to 150° C. (stirrer speed 250 rpm). The pressure in the autoclave increased to 67 bar. After 30 min, the stirrer was switched off and the autoclave was cooled to 15° C. Analysis of the liquid product by gas chromatography showed a methyl formate conversion of 92% with an essentially quantitative selectivity to methanol.

EXAMPLE 2

Example 1 was repeated except that 30 g of ethyl formate were used in place of methyl formate. During the course of the reaction the pressure in the autoclave increased to 63 bar. Analysis of the liquid product showed an ethyl formate conversion of 96% to ethanol.

EXAMPLE 3

Example 1 was repeated except that the autoclave was charged with 39 g of methyl formate, 0.8 g of propylene oxide and 1.5 g of 1,8-diazabicyclo[5.4.0]undec-7-ene (DBU). During the course of the reaction the pressure in the autoclave increased to 78 bar. Analysis of the liquid product showed a methyl formate conversion of 89%, with a selectivity to methanol of 99%.

EXAMPLE 4

Example 3 was repeated except that 1.5 g of 1,5-diazabicyclo[4.3.0]non-5-ene was used as a catalyst in place of DBU. Analysis of the liquid product showed a methyl formate conversion of 86% with a selectivity to methanol of 99%.

EXAMPLE 5

Example 3 was repeated except that 2.5 g of tributylphosphine was used as a catalyst in place of DBU and the amount of propylene oxide added was increased to 2.5 g. Analysis of the liquid product showed a methyl formate conversion of 8% to methanol.

EXAMPLE 6

Example 5 was repeated except that 4 g of methanol was also charged to the autoclave and the reaction was carried out at 140° C. for 10 minutes.

Analysis of the liquid product showed a methyl formate conversion of 80% to methanol. This example illustrates the benefit of having methanol present at the start of the reaction when the Lewis base used is a trivalent phosphorus compound.

EXAMPLE 7

The autoclave described in Example 1 was charged with 39 g of methyl formate, 1.2 g of triethylamine, and 2.1 g of propene oxide. It was sealed and pressurised to 15 bar with nitrogen, following which it was heated to 150° C. with stirring (250 rpm). The pressure in the autoclave increased to 76 bar. After one hour, the stirrer was switched off and the autoclave cooled to 15° C. Analysis of the liquid product showed a methyl formate conversion of 77% with a selectivity to methanol of 95%.

EXAMPLE 8

Example 7 was repeated except that 1 g of N-methyl imidazole was used as a catalyst in place of triethylamine. Analysis of the liquid product showed a methyl formate conversion of 79% with a selectivity to methanol of 96%.

I claim:

1. A process for the decarbonylation of an alkyl formate to form carbon monoxide and an alcohol at elevated temperature characterised in that the process is carried out in the presence of, as catalyst, an effective amount of:
    (a) a Lewis base and an epoxide or
    (b) an amidine.
2. A process as claimed in claim 1 characterised in that the catalyst is an amidine and the amidine is a guanidine.
3. A process as claimed in claim 1 characterized in that the catalyst is a cyclic amidine.
4. A process as claimed in claim 3 characterised in that the cyclic amidine is a guanidine.
5. A process as claimed in either claims 3 or 4 characterised in that the amidine group forms part of a fused ring system containing 6 and 5 membered rings or 6 and 7 membered rings or two six membered rings.
6. A process as claimed in claim 1 characterised in that the catalyst is a Lewis base and an epoxide and the Lewis base is an organic compound containing trivalent phosphorus or nitrogen.
7. A process as claimed in claim 1 characterised in that the catalyst is a Lewis base and an epoxide and the Lewis base is an amidine.
8. A process as claimed in claim 6 or 7 characterised in that the epoxide is a lower alkylene oxide.
9. A process as claimed in claim 1 characterised in that the catalyst is a Lewis base and an epoxide and the ratio of Lewis base to epoxide is in the range 1:0.5 to 1:5.
10. A process as claimed in claim 1 characterised in that an alcohol is present at the start of the process.
11. A process as claimed in claim 1 characterised in that the temperature is from 50° to 200° C. and the pressure 1 to 150 bar.

* * * * *

UNITED STATES PATENT AND TRADEMARK OFFICE
CERTIFICATE OF CORRECTION

PATENT NO. : 4,474,744
DATED : October 2, 1984
INVENTOR(S) : MICHAEL J. GREEN

It is certified that error appears in the above-identified patent and that said Letters Patent is hereby corrected as shown below:

Col. 1, line 52, "glass" should read --class-

Signed and Sealed this

Seventh Day of May 1985

[SEAL]

Attest:

DONALD J. QUIGG

Attesting Officer     Acting Commissioner of Patents and Trademarks